United States Patent [19]
Yasaka et al.

[11] Patent Number: 5,998,677
[45] Date of Patent: Dec. 7, 1999

[54] PROCESS FOR THE PRODUCTION OF PHENOL

[75] Inventors: Naoto Yasaka; Tatsuo Shirahata, both of Chiba, Japan

[73] Assignee: Mitsui Chemicals, Inc., Tokyo, Japan

[21] Appl. No.: 08/674,567

[22] Filed: Jul. 5, 1996

[30] Foreign Application Priority Data

Jul. 7, 1995 [JP] Japan .................................. 7-171923

[51] Int. Cl.⁶ ........................... C07C 37/08; C07C 45/53
[52] U.S. Cl. ............................................. 568/798; 568/768
[58] Field of Search .................................... 568/798, 768

[56] References Cited

U.S. PATENT DOCUMENTS

| | | |
|---|---|---|
| 4,358,618 | 11/1982 | Sifniades et al. . |
| 4,449,828 | 5/1984 | Mansour .................................. 366/147 |
| 5,245,090 | 9/1993 | DeCaria et al. ........................ 568/798 |
| 5,254,751 | 10/1993 | Zakoshansky .......................... 568/798 |
| 5,463,136 | 10/1995 | Blackbourn et al. ................... 568/385 |
| 5,530,166 | 6/1996 | Zakoshansky et al. ................. 568/798 |

FOREIGN PATENT DOCUMENTS 251408  11/1990  Japan .

*Primary Examiner*—Jeffrey C. Mullis
*Attorney, Agent, or Firm*—Birch, Stewart, Kolasch & Birch, LLP

[57] ABSTRACT

The improved process for producing phenol, acetone and α-methylstyrene in the cumene-phenol process comprising cumene hydroperoxide, cumene and dimethylphenylcarbinol in the presence of sulfuric acid has the steps of decomposing the cumene hydroperoxide in a back mixing reactor with the yield of α-methylstyrene as produced from dimethylphenylcarbinol being controlled and the step of forming α-methylstyrene in such a way that the reaction mixture produced in the first step is supplied into a plug-flow reactor after acetone is added to said reaction mixture. The process is capable of consistent production of phenol and α-methylstyrene in high yields under mild reaction conditions.

10 Claims, No Drawings

PROCESS FOR THE PRODUCTION OF PHENOL

FIELD OF THE INVENTION

This invention relates to a process for the production of phenol which is useful as an intermediate for the manufacture of synthetic resins, agrichemicals, dyes, pharmaceuticals, etc.

DESCRIPTION OF THE RELATED ARTS

There have been proposed various processes for producing phenol and one of the most commonly used processes is the cumene-phenol process which starts with cumene to synthesize phenol. In this process, cumene is oxidized with oxygen or air to produce cumene hydroperoxide (hereunder abbreviated as "CHP") which is cleaved to phenol and acetone in the presence of an acid catalyst. The main products of the cumene-phenol process are phenol and acetone. In addition, dimethylphenylcarbinol (hereunder "DMPC") is formed as a by-product in the cumene oxidation reaction, and then DMPC is dehydrated in the acid cleavage of CHP to give α-methylstyrene (hereunder "α-MS") as a by-product. The α-MS is readily hydrogenated back to cumene which is reusable as a raw materials. The α-MS is also industrially useful as a resin modifier.

In this process, various side-reactions take place that will lower the yields of phenol (which is one of the end products of CHP cleavage reaction), α-MS, etc. as exemplified by the reaction between α-MS and phenol to produce cumylphenol and the dimerization of α-MS to produce a methyl styrene dimer. Another by-product of the CHP cleavage reaction is a very small amount of hydroxyacetone (hereunder "HA"). The HA is difficult to separate from phenol by distillation and can deteriorate the quality of the phenol if it is present in this otherwise pure final product. If bisphenol A is manufactured from a phenol containing HA, a colored product will result that is very low in commercial value. What is more, the HA is water-soluble and has such a high COD load that it dissolves in the effluent from the cumene-phenol process, making the biological or other treatment of the effluent necessary.

Among these problems, the side reactions that lower the yields of phenol and α-MS have been addressed by the proposal of a method for performing acid cleavage of CHP after it is diluted with a solvent such as acetone (see, for example, Examined Japanese Patent Publication Nos. 3875/1952 and 4619/1953) or a method of carrying out the reaction in more than one stage (see, for example, U.S. Pat. No. 2,757,209 and Examined Japanese Patent Publication No. 13464/1962). According to the references that teach the first proposal, the side reactions are controlled by the diluting effect of the solvent and the improved efficiency of contact between the acid catalyst and CHP. The second proposal described in U.S. Pat. No. 2,757,209 is to perform the CHP cleavage reaction in multi stages; in the first stage, the acid cleavage reaction is carried out under mild conditions at a lower acid catalyst concentration and a lower temperature than in the conventional method of completing the reaction for the production of phenol and α-MS in one stage, such that a few percent of CHP is left in the product; in the second stage, the product of the first-stage reaction is introduced into a plug-flow reactor for cleaving the organic peroxides in the product and for dehydration of DMPC.

Methods to prevent contamination of an otherwise pure phenol with HA are described in BP 1,231,991, U.S. Pat. No. 5,064,507, etc. According to BP 1,231,991, the product of cumene oxidation which is chiefly composed of CHP is subjected to acid cleavage reaction and the reaction mixtures are distilled to separate a crude phenol from acetone, low-boiling point components (e.g. hydrocarbons) and high-boiling point components (e.g. unreacted DMPC, cumylphenol and methylstyrene dimer); the crude phenol is treated with an cation-exchange resin such that the HA in the crude phenol is converted to an easily separable high-boiling impurities, which is thereafter separated from the crude phenol by distillation. According to U.S. Pat. No. 5,064,507, the crude phenol is treated with an organic polyamine, whereupon the HA in the crude phenol reacts with the added organic polyamine to form a high-boiling point compound, which is then separated from the crude phenol with a distillation column.

However, these methods simply complicate the process of phenol manufacture and require an expensive facility for HA removal. Thus, controlling the production of cumylphenol, methylstyrene dimer and other high-boiling point components that will lower the yields of the end products, as well as the production of HA which will deteriorate the quality of the pure phenol is critical to the commercial implementation of the cumene-phenol process.

Examined Japanese Patent Publication No. 51408/1990 teaches a two-stage process. In the first stage, a back mixing reactor is used to perform the reaction at a sulfuric acid concentration of 30–100 ppm and at a temperature of 50–90° C. such that the concentration of CHP in the reaction mixture is reduced to 0.5–5 wt %. In the first-stage reaction, the conversion of DMPC to dicumyl peroxide (hereunder "DCP") is at least 40%. The product of the first-stage reaction is then sent to a plug-flow reactor, where the second-stage reaction is carried out at 120–150° C. to cleave the DCP produced in the first-stage reaction.

U.S. Pat. No. 5,254,751 teaches another two-stage process. In the first stage, the reaction is carried out in a non-isothermal reactor at an acid catalyst concentration of 150–500 wt.ppm and at a temperature of 50–62° C. in the presence of added acetone such that the concentration of CHP is lowered to 0.3–1.5%. After being mixed with aqueous ammonia, the product of the first-stage reaction is sent to a plug-flow reactor and the second-stage reaction is carried out at a temperature of 80–110° C. to cleave the DCP produced in the first-stage reaction.

A critical problem with the reaction for the acid catalized cleavage of CHP is that the reaction rate is very fast, with the half life being only a few seconds, and that the heat of the resulting cleavage reaction is several times as great as what develops in common exothermic reactions of organic chemistry. Therefore, if a few percent of CHP is cleaved momentarily due to changes in the reaction conditions, the temperature of the reaction mixture will rise sharply and acetone which is a low-boiling point component of the reaction mixture will evaporate to increase the pressure in the reactor, potentially causing the reactor to burst. Hence, for the success of the multi-stage process in which unreacted CHP remains in the first-stage reactor, it is desired that the process be operated under stable conditions and that yet the end products be obtained in high yields.

SUMMARY OF THE INVENTION

An object, therefore, of the present invention is to provide a process by which both phenol and α-MS can be produced consistently in high yield under mild reaction conditions with controlled HA formation.

With a view to attaining this object, the present inventors conducted intensive studies on the aforementioned problems with the adoption of the multi-stage method in the cumene-phenol process. As a result, they found that the cumylphenol and methylstyrene dimer which would reduce the yields of phenol and α-MS were more likely to be formed with the increasing concentration of α-MS in the reaction mixture. Stated more specifically, the reaction mixture in a back mixing reactor has a uniform composition, so that the composition of the reaction mixture within the reactor is identical to that at the exit of the reactor. Hence, performance of the reaction for producing α-MS from DMPC within the back mixing reactor gives a high concentration of α-MS in the reactor. The present inventors found that this caused an increased production of cumylphenol and methylstyrene dimer both of which were heavier forms of α-MS. The inventors found that in order to control the formation of cumylphenol and methylstyrene dimer, it was preferable to carry out the α-MS forming reaction in a plug-flow reactor which would allow the reaction mixture to change composition with the progress of the reaction, namely, a reactor of the type that would create a non-uniform composition. Better results were attained by diluting the reaction mixture with a solvent. A preferred solvent is acetone which has the lowest boiling point of the main components of the reaction mixture and it was found to be economical to circulate the solvent between the reactor in the subsequent stage and the distillation column.

As already mentioned in connection with the prior art, HA is difficult to separate from phenol by distillation and will deteriorate the quality of the phenol if it contaminates the otherwise pure final product. This HA is produced from acetone in the presence of CHP. Acetone is formed in a molar amount equal to that of CHP which is being cleaved with an acid catalyst and, hence, it is difficult to ensure that HA will not be formed at all. However, the present inventors found that the formation of HA could be reduced by carrying out the acid cleavage of CHP at a low acetone concentration, namely, without addition of the acetone separated in the distillation zone.

Based on these findings, the present inventors concluded that in order to produce phenol, acetone and α-MS from the product of cumene oxidation efficiently while controlling the formation of HA which would deteriorate the quality of otherwise pure phenol, it was preferable to divide the reaction into two or more stages and perform the respective reactions under appropriate conditions.

Accordingly, in order to attain the above-stated object, the present invention provides a process for producing phenol, acetone and α-methylstyrene from the product of cumene oxidation comprising cumene hydroperoxide, cumene and dimethylphenylcarbinol in the presence of sulfuric acid, characterized by comprising the step of decomposing the cumene hydroperoxide in a back mixing reactor with the yield of α-methylstyrene as produced from dimethylphenylcarbinol being controlled to no more than 35%, and the step of forming α-methylstyrene in such a way that the reaction mixture produced in the first step is supplied into a plug-flow reactor after acetone is added to said reaction mixture.

DETAILED DESCRIPTION OF THE INVENTION

The process of the invention for producing phenol (which is hereunder referred to simply as the "invention process") will now be described in detail.

The invention process is for producing phenol, acetone and α-MS from the product of cumene oxidation containing CHP as the main component by a multi-stage scheme that consists of a first-stage reaction intended primarily for performing acid catalyzed cleavage of CHP in a back mixing reactor and a second-stage reaction intended primarily for producing α-MS in a plug-flow reactor.

In the first stage of the invention process, CHP which is the main component of the starting material (i.e., the product of cumene oxidation) is cleaved to phenol and acetone in a back mixing reactor in the presence of sulfuric acid. The product of cumene oxidation which is supplied as the starting material is prepared by first oxidizing cumene with air or oxygen at a temperature of about 100° C. in the presence of sodium carbonate and then separating the unreacted cumene from the oxidation product to give a specified CHP concentration in a distillation column. The product of cumene oxidation has typically the following composition:

| CHP | 65–85 wt % |
|---|---|
| DMPC | 2–10 wt % |
| Cumene | 15–35 wt % |
| Acetophenone | 0.2–2 wt % |

The first-stage reaction to be carried out in the invention process is for producing phenol and acetone from CHP while controlling the formation of α-MS and HA. In this first-stage reaction, the conversion of CHP is desirably in the range of 97–99.5%, preferably 98–99.0%, and the yield of α-MS as produced from the dimethylphenylcarbinol in the product of cumene oxidation is desirably not more than 35%, preferably no more than 30%. The reaction conditions are desirably mild as exemplified by a sulfuric acid concentration of 150–300 wt.ppm and a reaction temperature of 55–80° C. According to the teaching of Examined Japanese Patent Publication No. 9971/1958, the temperature for carrying out the reactions for the acid catalized cleavage of CHP and the formation of α-MS is preferably in the range of 50–80° C. If the temperature for carrying out the reaction for the acid catalized cleavage of CHP in the present invention is higher than specified in Examined Japanese Patent Publication No. 9971/1958, thermal decomposition of CHP will occur, leading to lower yields of phenol and acetone. If the reaction temperature is unduly low, an expensive facility is required to remove the heat of reaction and, in addition, temperature instability occurs during continuous reaction. The invention process adopts a lower concentration of sulfuric acid than the method described in Examined Japanese Patent Publication No. 9971/1958, the optimal temperature range for the invention process is narrower than the temperature range described in said patent publication.

In the invention process, the water concentration for carrying out the reactions for the acid catalyzed cleavage of CHP and the formation of α-MS is preferably in the range from 0.5 to 3 wt %. As already described in Examined Japanese Patent Publication No. 9971/1958, the water concentration for carrying out the reaction need to be so adjusted as to provide a uniform reaction mixture. Even if the reaction mixture is uniform, an unduly high water concentration will lower the acid strength of the sulfuric acid used as a catalyst, thus increasing the concentration of CHP in the reactor. Hence, it is not preferable to employ a water concentration higher than the upper limit specified for the practice of the invention process.

Thus, compared to the one-stage scheme for carrying out the reactions for the acid catalized cleavage of CHP and the formation of α-MS, the first-stage reaction to be carried out in the invention process adopts a mild condition characterized by low sulfuric acid concentration; as a result, the DMPC which is existing as a by-product in the starting cumene oxidation is either converted to DCP which is the product of reaction with CHP or present unreacted in the reaction mixture, thereby controlling the conversion of DMPC to α-MS.

During prolonged operations of a large system in a commercial plant, the reaction conditions will normally vary more or less. Even if such variations occur, the compositional change in the reaction mixture must be held to a minimum. The operational stability of the process to produce phenol and acetone from CHP is affected by the variations in the acid strength of the catalyst and the reaction temperature. The acid strength of the catalyst is susceptible not only to the increase in the concentration of water in the reaction solution but also to the concomitant sodium salt in the starting cumene oxidation product and a lower acid strength will retard the cleavage of CHP, thereby causing it to accumulate in the reactor. Therefore, in order to reduce the effects of variations in the process conditions and thereby ensuring that the concentration of CHP in the reaction product is kept constant, the reaction has to be carried out with the acid catalyst concentration being held to no less than 100 wt.ppm, preferably no less than 150 wt.ppm. An acid catalyst concentration in the range from 30 to 100 wt.ppm is so low that it would be difficult to ensure stable plant operation for a prolonged time.

The residence time of the reaction mixture in the back mixing reactor is from 5 to 40 minutes and typically adjusted to be in the range from about 15 to about 30 minutes.

The heat of reaction that develops when CHP is cleaved with an acid to produce phenol and acetone in the first-stage reaction is several times as great as the heat of normal reactions in organic chemistry. Therefore, in the first-stage reaction, the temperature in the back mixing reactor must be controlled such that the heat of reaction produced is completely removed to maintain a specified reaction temperature, whereby the rate of CHP cleavage is held constant to insure that the reaction mixture of a stable composition emerges from the exit of the back mixing reactor to enter the second-stage reactor. To this end, the back mixing reactor need be an apparatus suitable for controlling the temperature in the reactor to be constant. For controlling the reaction temperature to be constant, it is preferable to adopt the acetone reflux method in which the pressure in the reactor is lowered to the vapor pressure of the reaction mixture and the latent heat of evaporation of the volatilized acetone is removed so as to maintain the temperature in the reactor at a constant level; alternatively, part of the reaction mixture in the reactor is withdrawn and passed through a cooling heat exchanger so that the developing heat of reaction is removed before it is returned to the reactor.

In the invention process, the reaction mixture emerging from the back mixing first-stage reactor to be subjected to the second-stage reaction contains phenol, acetone, DMPC, DCP and cumene as a main ingredient. This reaction mixture is supplied to a plug-flow reactor for carrying out the second-stage reaction, primarily for producing α-MS from the DMPC or DCP in the reaction mixture.

In the invention process, the second-stage reaction is performed with acetone being added in order to control the reaction that will produce cumylphenol or methylstyrene dimer from α-MS. The acetone to be added is preferably of a type that is recovered by a separator such as a distillation column from the reaction product leaving the plug-flow reactor after the end of the second-stage reaction and which is returned to the same plug-flow reactor.

The amount of acetone to be added in the second-stage reaction should be 1.15–1.8 times as much as the acetone concentration in the first-stage reaction.

The purpose of adding acetone in the second-stage reaction is to lower the concentration of α-MS in the second-stage reactor, thereby controlling the reaction that yields heavier forms of α-MS and which will lower the yields of phenol and α-MS. As just mentioned above, the amount of acetone added for this purpose should be 1.15–1.8 times as much as the acetone concentration in the first-stage reaction. Adding a greater amount of acetone is effective in further controlling the reaction which produces heavier forms of α-MS but, on the other hand, more acetone need be circulated between the reactor and the acetone distillation column, causing a corresponding increase in the energy consumption for distilling acetone and a disadvantage rather than an advantage will result in view of overall process economy. If the addition of acetone is unduly small, it is hardly effective in controlling the reaction that produces heavier forms of α-MS.

In the invention process, the production of heavier forms of α-MS is not likely to occur in the first-stage reaction. This can be explained as follows: in the first-stage reaction, the concentration of sulfuric acid used as a catalyst is so low that DMPC will undergo dehydrative condensation reaction with CHP to form DCP and dehydration to α-MS is less likely to occur. As a result, the concentration of α-MS in the back mixing reaction is low enough to ensure that the reaction for producing heavier forms of α-MS is practically unlikely to occur. Therefore, if acetone is added in the first-stage reaction, its effectiveness in controlling the reaction that produces heavier forms of α-MS is no different from the effectiveness of adding acetone in the second-stage reaction. In other words, the yields of phenol and α-MS that are produced when acetone is added in the first-stage reaction are substantially comparable to the yields obtained by adding acetone in the second-stage reaction. As already mentioned in connection with the prior art, an unduly high acetone concentration in the reaction for the acid cleavage of CHP increases the production of HA which will deteriorate the otherwise pure phenol. The first-stage reaction to be performed in the invention process is intended primarily for effecting the acid cleavage of CHP, the addition of acetone in the first-stage reaction will increase the HA production, thereby deteriorating the otherwise pure phenol.

On the other hand, the second-stage reaction is intended primarily for producing α-MS and the acid cleavage of CHP in effect will not occur; therefore, there will be no increase in HA production even if acetone is added in the second-stage reaction. Consequently, the yields of phenol and α-MS that are produced when acetone is added in the second-stage reaction are comparable to those attained by the adding acetone in the first-stage reaction and yet a smaller amount of HA is produced.

The reaction mixture to which acetone is added is passed through a heat exchanger such that it is heated to 80–100° C. before it is supplied into an adiabatic plug-flow reactor.

If the temperature for the second-stage reaction is elevated, the reaction rate is increased, making it necessary to shorten the reaction time. In the case where the temperature for the second-stage reaction exceeds 120° C., the rate of by-producing of cumyl phenol and methylstyrene dimer which are heavier forms of α-MS will increase abruptly if the conversion of DCP and DMPC to α-MS is 70% or more. Therefore, if the reaction for α-MS formation is carried out at temperatures higher than the upper limit for the second-stage reaction in the invention process, the range that permits appropriate control of the reaction becomes so narrow that there may be considerable difficulty in controlling prolonged operations at commercial plants.

The second-stage reaction for producing α-MS from DP is exothermic, so if it is performed in an adiabatic plug-flow reactor, a non-isothermal state will be dominant in the reactor, causing the temperature at the exit of the reactor to be higher than the entrance temperature. Stated more specifically, the temperature difference between the entrance and exit of the reactor, which varies with the amount of DCP that undergoes the second-stage reaction, is typically from about 8 to about 20° C. The temperature at the exit of the second-stage reactor is desirably no more than 120° C., preferably no more than 115° C. and it is necessary that the elevation of the temperature of the reaction mixture in the first-stage reaction be so adjusted that the temperature of the reaction mixture at the exit of the second-stage reactor will not exceed the above-specified upper limit.

It is also necessary to ensure against back mixing of the reaction mixture in the plug-flow second-stage reactor by increasing its length compared to the inside diameter or by providing baffle plates within the reactor. The residence time of the reaction mixture in the second-stage plug-flow reactor is typically from about 5 to about 30 minutes, preferably from about 8 to about 20 minutes.

If the second-stage reaction for the production of α-MS from DCP and DMPC ends in the plug-flow reactor in the invention process, the reaction is quenched by immediately cooling the reaction mixture and neutralizing the sulfuric acid used as the acid catalyst. If the acid catalyst remains in the reaction mixture, the reaction that produces heavier forms of α-MS (i.e., cumylphenol and methylstyrene dimer) will continue even after the end of the reaction for the cleavage of organic peroxides and this will lower the yields of α-MS and phenol. To avoid this problem, the acid catalyst must be neutralized as soon as the reaction for the cleavage of organic peroxides ends.

The sulfuric acid which is the acid catalyst in the reaction mixture can be neutralized in accordance with a method that uses either sodium hydroxide or sodium carbonate or sodium phenolate which is a salt of sodium hydroxide with phenol.

The neutralized reaction product is then subjected to distillation so that it is separated into acetone, phenol, α-MS, cumene, etc. A part of the separated acetone is recycled for use as a diluent in the second-stage reaction. The distillation of the neutralized reaction product is performed with a distillation column under atmospheric or subatmospheric pressure conditions.

The crude acetone produced in the cumene-phenol process for phenol manufacture contains aldehydes, alcohols, water, etc. Among these components, aldehydes and water are difficult to separate by distillation and much energy is consumed by the purifying operation. Therefore, the use of purified acetone as a diluent for the reaction mixture is not economical and adds to the cost of phenol manufacture. If, on the other hand, crude acetone is used as a diluent for the reaction mixture in the second-stage reaction, the aldehydes in the crude acetone will be converted to heavier forms as catalyzed by the sulfuric acid in the reaction mixture, so that it is recycled at a given concentration without building up in the distillation path.

The concentration of aldehydes in the crude acetone for use as a diluent of the reaction mixture in the second-stage reaction ranges from 100 to 5,000 wt.ppm, preferably from 500 to 2,500 wt.ppm. The concentration of water in the crude acetone ranges from 0.3 to 3 wt %, preferably from 1 to 2 wt %. If the concentration of aldehydes or water in the crude acetone drops, there occurs a marked increase in the energy consumption required by the distilling operation. If, on the other hand, the concentration of aldehydes or water in the crude acetone increases, the reaction mixture diluted in the second-stage reaction will contain an increased amount of water and then the reaction efficiency will be decreased.

SPECIFIC EXAMPLES OF THE INVENTION

The following examples and comparative examples are provided for the purpose of further illustrating the present invention but are in no way to be taken as limiting.

Example 1

Cumene was oxidized with air at 70–115° C. in the presence of sodium carbonate, followed by oil-water separation and concentrating to prepare the product of cumene oxidation, which had the following composition:

| CHP | 81.0 wt % |
|---|---|
| DMPC | 5.2 wt % |
| Acetophenone | 0.8 wt % |
| Cumene | 13.0 wt % |

The product of cumene oxidation was supplied into a multi-stage reaction system composed of a continuous type back mixing reactor having a heat removing capability and an adiabatic plug-flow reactor. In the multi-stage reaction system, two reactions were performed sequentially, the cleavage of CHP in the first stage and the formation of α-MS in the second stage.

The first-stage reaction was carried out at a temperature of 60° C. and at a sulfuric acid concentration of 200 wt.ppm for a residence time of 20 minutes. The temperature in the first-stage reactor was kept constant by removing the heat of the reaction mixture while agitating it. An aqueous solution of 5% sulfuric acid was added continuously to ensure that the concentration of sulfuric acid in the reactor would be held at 200 ppm. As a result, the conversion of CHP to another component was 98.9% and the yield of α-MS as produced from DMPC was 18.0%.

Subsequently, acetone was added in an amount 1.4 times the concentration of acetone in the first-stage reaction mixture. The added acetone had been separated from the neutralized product of the second-stage reaction by distillation and it contained 1,000 wt.ppm of an aldehyde having a lower boiling point than acetone and 1.8 wt % of water. The first-stage reaction mixture was then heated in a heat exchanger and supplied into a plug-flow reactor for carrying out the second-stage reaction. The residence time of the reaction mixture in the second-stage reactor was 10 minutes; the temperature at the exit of the second-stage reactor was 110° C.; and the second-stage reaction mixture had a water concentration of 1.0 wt %. The final reaction product was analyzed to determine the yields of phenol and α-MS, as well as the concentration of HA. The results are shown in Table 1 below.

TABLE 1

| Phenol yield | 98.3% |
|---|---|
| α-MS yield | 82.8% |
| HA concentration | 680 wt. ppm |

Phenol yield =

$$\frac{\text{Phenol in the reaction product (mol/h)}}{\text{CHP in the starting cumene oxidation product (mol/h)}} \times 100$$

α-MS yield =

$$\frac{\text{a-MS in the reaction product (mol/h)}}{\text{DCPM in the starting cumene oxidation product (mol/h)}} \times 100$$

HA concentration: Amount of HA produced per unit feed of the starting cumene oxidation product

Example 2

The product of cumene oxidation as prepared in Example 1 was subjected to reactions in a reaction system of the same type as used in Example 1. The first-stage reaction was carried out at a temperature of 60° C. and at a sulfuric acid concentration of 250 wt.ppm for a residence time of 15 minutes. An aqueous solution of 5% sulfuric acid was supplied continuously to ensure that the concentration of sulfuric acid in the reactor would be held at 250 wt.ppm. The conversion of CHP to another component in the first-stage reaction was 98.7% and the yield of α-MS as produced from DMPC was 16.2%.

Subsequently, acetone was added in an amount 1.54 times the concentration of acetone in the first-stage reaction mixture. The added acetone had been separated from the neutralized product of the second-stage reaction by distillation and it contained 1,000 wt.ppm of an aldehyde having a lower boiling point than acetone and 1.8 wt % of water. The first-stage reaction mixture was then heated in a heat exchanger and supplied into a plug-flow reactor for carrying out the second-stage reaction. The residence time of the reaction mixture in the second-stage reactor was 21 minutes; the temperature at the exit of the second-stage reactor was 113° C.; and the second-stage reaction mixture had a water concentration of 1.4 wt %. The second-stage reaction product was analyzed to determine the yields of phenol and α-MS, as well as the concentration of HA. The results are shown in Table 2 below.

TABLE 2

| Phenol yield | 98.4% |
|---|---|
| α-MS yield | 83.6% |
| HA concentration | 700 wt · ppm |

Example 3

The product of cumene oxidation as prepared in Example 1 was subjected to reactions in a reaction system of the same type as used in Example 1. The first-stage reaction was carried out at a temperature of 75° C. and at a sulfuric acid concentration of 120 wt.ppm for a residence time of 15 minutes. An aqueous solution of 2.5% sulfuric acid was supplied continuously to ensure that the concentration of sulfuric acid in the reactor would be held at 150 wt.ppm. The conversion of CHP to another component in the first-stage reaction was 99.1% and the yield of α-MS as produced from DMPC was 21.0%.

Subsequently, acetone was added in an amount 1.54 times the concentration of acetone in the first-stage reaction mixture. The added acetone had been separated from the neutralized product of the second-stage reaction by distillation and it contained 1,000 wt.ppm of an aldehyde having a lower boiling point than acetone and 1.8 wt % of water. The first-stage reaction mixture was then heated in a heat exchanger and supplied into a plug-flow reactor for carrying out the second-stage reaction. The residence time of the reaction mixture in the second-stage reactor was 17 minutes; the temperature at the exit of the second-stage reactor was 108° C.; and the second-stage reaction mixture had a water concentration of 1.4 wt %. The second-stage reaction product was analyzed to determine the yields of phenol and α-MS, as well as the concentration of HA. The results are shown in Table 3 below.

TABLE 3

| Phenol yield | 98.2% |
|---|---|
| α-MS yield | 84.1% |
| HA concentration | 640 wt · ppm |

Comparative Example 1

The product of cumene oxidation as prepared in Example 1 was subjected to reactions in a reaction system of the same type as used in Example 1. Acetone was added to the first-stage reaction mixture but no acetone was added in the second-stage reaction. The first-stage reaction was carried out at a temperature of 75° C. for a residence time of 15 minutes. A solution containing 2,000 wt.ppm of acetone sulfite was supplied continuously to ensure that the concentration of sulfuric acid in the reactor would be held at 260 wt.ppm. The added acetone had been separated from the neutralized product of the second-stage reaction by distillation and it contained 1,000 wt.ppm of aldehyde having a lower boiling point than acetone and 1.8 wt % of water. The acetone concentration of the reaction mixture was 1.3 times as high as the value for the case where no acetone was added. The conversion of CHP to another component in the first-stage reaction was 98.5% and the yield of α-MS as produced from DMPC was 29.0%.

Subsequently, the first-stage reaction mixture was heated in a heat exchanger and supplied into a plug-flow reactor for carrying out the second-stage reaction. The residence time of the reaction mixture in the second-stage reactor was 17 minutes; the temperature at the exit of the second-stage reactor was 108° C.; and the second-stage reaction mixture had a water concentration of 1.4 wt %. The second-stage reaction product was analyzed to determine the yields of phenol and α-MS, as well as the concentration of HA. The results are shown in Table 4 below.

TABLE 4

| Phenol yield | 98.1% |
|---|---|
| α-MS yield | 80.6% |
| HA concentration | 1,100 wt · ppm |

Comparative Example 2

The product of cumene oxidation as prepared in Example 1 was subjected to reactions in a reaction system of the same type as used in Example 1. The first-stage reaction was carried out at a temperature of 70° C. and at a sulfuric acid concentration of 500 wt.ppm for a residence time of 20 minutes. An aqueous solution of 5% sulfuric acid was supplied continuously to ensure that the concentration of sulfuric acid in the reactor would be held at 500 wt.ppm. The conversion of CHP to another component in the first-stage reaction was 99.7% and the yield of α-MS as produced from DMPC was 39.4%.

Subsequently, acetone was added in an amount 1.54 times the concentration of acetone in the first-stage reaction mixture. The added acetone had been separated from the neutralized product of the second-stage reaction by distillation and it contained 1,000 wt.ppm of an aldehyde having a lower boiling point than acetone and 1.8 wt % of water. The first-stage reaction mixture was then heated in a heat exchanger and supplied into a plug-flow reactor for carrying out the second-stage reaction. The residence time of the reaction mixture in the second-stage reactor was 17 minutes; the temperature at the exit of the second-stage reactor was 105° C.; and the second-stage reaction mixture had a water concentration of 1.7 wt %. The second-stage reaction product was analyzed to determine the yields of phenol and α-MS, as well as the concentration of HA. The results are shown in Table 5 below.

TABLE 5

| Phenol yield | 97.7% |
|---|---|
| α-MS yield | 78.1% |
| HA concentration | 870 wt · ppm |

Thus, according to the invention process, phenol and α-MS can be manufactured in high yields with reduced formation of HA and besides the manufacturing operation is very stable. Therefore, the invention process is of great value in practical applications.

We claim:

1. An improved process for producing phenol, acetone and α- methylstyrene from the product of cumene oxidation using a single back mixing reactor and a single plug flow reactor, said process comprising in a first stage back mixing reactor reacting cumene hydroperoxide, cumene and dimethylphenylcarbinol in the presence of sulfuric acid, said improved process comprising the steps of:

(1) cleaving the cumene hydroperoxide in a first stage back-mixing reactor, in the presence of 150–350 wt.ppm of sulfuric acid based on the product of cumene oxidation, to form a reaction mixture of phenol and acetone having 0.5–3.0 wt % $H_2O$ while controlling the temperature in said first stage back mixing reactor at 55–80° C. by:

(a) withdrawing a part of the reaction mixture and passing the part to a heat exchanger and thus removing the heat of reaction for the cleavage of the cumene hydroperoxide in the heat exchanger and recycling the part of the reaction mixture to the first stage back mixing reactor, or (b) by lowering the pressure in said back mixing reactor to the vapor pressure of the reaction mixture, thereby removing the latent heat of evaporation of the volatilized acetone and then returning the resultant liquefied acetone into the back mixing reactor;

(2) controlling the yield of α-methylstyrene in said first stage reactor to no more than 35%;

(3) adding acetone to the output of the reaction mixture produced in the first stage reactor in such an amount that the acetone concentration is 1.15–1.8 times as much as in the reaction mixture produced from the first stage reactor;

(4) without diverting the first stage reaction mixture with added acetone supplying the resultant reaction mixture from step (3) into the plug-flow second stage reactor without hydrogenation in said plug-flow reactor; and (5) separating and recovering α-methylstyrene from said plug-flow second stage reactor.

2. The process according to claim 1, wherein the cleavage of the cumene hydroperoxide is performed to give 97–99.5% conversion of the cumene hydroperoxide.

3. An improved process for producing phenol using a single back mixing reactor and a single plug flow reactor which comprises:

(1) cleaving cumene hydroperoxide in a first stage back mixing reactor in the presence of sulfuric acid and controlling the yield of α-methylstyrene as produced from dimethylphenylcarbinol to no more than 35%, by weight of the reaction mixture output from the first stage, (2) adding acetone to the resultant output of the reaction mixture from the first stage reactor, and then without diverting the first stage reaction mixture with added acetone supplying the so-obtained reaction mixture into the plug-flow second stage reactor and dehydrating the dimethylphenylcarbinol and cleaving the cumene hydroperoxide, in the second stage reactor without hydrogenation, and (3) separating and recovering phenol from the output of the second stage reactor.

4. The process according to claim 3, wherein after the addition of the acetone to the resultant output of reaction mixture from the first stage reactor, said reaction mixture is heated to 80–100° C. in a heat exchanger.

5. The process according to claim 4, wherein the thus heated reaction mixture is supplied into the second stage plug-flow reactor in a non-isothermal state for producing α-methylstyrene from the dimethylphenylcarbinol and dicumyl peroxide.

6. The process according to claim 3, wherein the temperature of the reaction mixture at the exit of the second stage plug-flow reactor is no more than 120° C.

7. The process according to claim 3, wherein the temperature of the reaction mixture at the exit of the second stage plug-flow reactor is no more than 115° C.

8. The process according to claim 3, wherein the reaction mixture emerging from the second stage plug-flow reactor is immediately cooled and neutralized to stop the reaction.

9. The process according to claim 8, wherein acetone is separated from the reaction mixture output from the second stage plug-flow reactor with a distillation column after the reaction is stopped and wherein at least part of the separated acetone is recycled to the reaction mixture output from the first stage complete back-mixing reactor in such an amount that the acetone concentration of said reaction mixture output is 35–50 wt % before said reaction mixture output is supplied into the second stage plug-flow reactor.

10. The process according to claim 9, wherein the acetone to be added to the reaction mixture from the first stage back-mixing reactor contains 100–5,000 wt.ppm of an aldehyde and 0.3–3 wt % of water.

* * * * *